US006319707B1

(12) United States Patent
Adam et al.

(10) Patent No.: US 6,319,707 B1
(45) Date of Patent: Nov. 20, 2001

(54) CAP-INDEPENDENT MULTICISTRONIC RETROVIRAL VECTORS

(75) Inventors: Mohammed A. Adam, Kirkland (CA); A. Dusty Miller; William Reginald Alfred Osborne, both of Seattle, WA (US)

(73) Assignee: Fred Hutchinson Cancer Research Center Board Regents of the University of Washington, Seattle, WA (US)

( * ) Notice: Subject to any disclaimer, the term of this patent is extended or adjusted under 35 U.S.C. 154(b) by 0 days.

(21) Appl. No.: 08/009,338

(22) Filed: Jan. 26, 1993

Related U.S. Application Data

(63) Continuation of application No. 07/743,513, filed on Aug. 12, 1991, now abandoned.

(51) Int. Cl.[7] .......................... C12N 15/63; C12N 15/85; C12N 15/11; C07H 21/04

(52) U.S. Cl. .................... 435/320.1; 435/325; 536/23.1; 536/24.1

(58) Field of Search .............................. 435/235.1, 240.1, 435/240.2, 320.1, 325; 536/23.1, 24.1

(56) References Cited

PUBLICATIONS

D.D.L. Bowtell et al (1988) J. Virol 62(7):2464–2473.*
J R. McLachlin et al (1990) Progress in Nucleic Acid Research and Molecular Biology 38:91–135.*
Osborne, W.R.A., et al., Long–term expression of human adenosine deaminase in rats after transplantation of genetically–modified vascular smooth muscle cells, *Int. J. Purine Pyrimidine Res.*, vol. 2, Suppl. 1, 1991.
Hock, R.A., A.D. Miller, and W.R.A. Osborne 1989. Expression of human adenosine deaminase from various strong promoters after gene transfer into human hematopoietic cell lines. Blood 74:876–881.
Jang, S.K., M.V. Davies, R.J. Kaufman, and E. Wimmer. 1989. Initiation of protein synthesis by internal entry of ribosomes into the 5' nontranslated region of encephalomyocarditis virus RNA in vivo. J. Virol. 63:1651–1660.
Jang, S.K., H.G. Krausslich, M.J. Nicklin, G.M. Duke, A.C. Palmenberg, and E. Wimmer. 1988. A Segment of the 5' nontranslated region of encephalomyocarditis virus RNA directs internal entry of ribosomes during in vitro translation. J. Virol. 62:2636–2643.
Jang, S.K., and E. Wimmer. 1990. Cap–independent translation of encephalomyocarditis virus RNA: structural elements of the internal ribosomal entry site and involvement of a cellular 57–kD RNA–binding protein. Genes Dev. 4:1560–1572.
Kozak, M. 1989. The scanning model for translation: an update. J. Cell Biol. 108:229–241. poliovirus RNA: implications for internal translation initiation. Genes Dev. 3:1026–1034.
Meerovitch, K., J. Pelletier, and N. Sonenberg. 1989. A cellular protein that binds to the 5'–noncoding region of
Miller, A.D. 1990. Retrovirus packaging cells. Human Gene Therapy 1:5–14.
Miller, A.D., D.R. Trauber, and C. Buttimore. 1986. Factors involved in the production of helper virus–free retrovirus vectors. Somat. Cell Mol. Genet. 12:175–183.
Peabody, D.S., and P Berg. 1986. Termination–reinitiation occurs in the translation of mammalian cell mRNAs. Mol. Cell. Biol. 6:2695–2703.
Peabody, D.S., S. Subramani, and P. Berg. 1986. Effect of upstream reading frames on translation efficiency in simian virus 40 recombinants. Mol. Cell. Biol. 6:2704–2711.
Pelletier, J., M.E. Flynn, G. Kaplan, V. Racaniello, and N. Sonenberg. 1988. Mutational analysis of upstream AUG codons of poliovirus RNA. J. Virol. 62:4486–4492.
Pelletier, J., G. Kaplan, V.R. Racaniello, and N. Sonenberg. 1988. Cap–independent translation of poliovirus mRNA is conferred by sequence elements within the 5'noncoding region. Mol. Cell. Biol. 8:1103–1112.
Pelletier, J., and N. Sonenberg. 1988. Internal initiation of translation of eukaryotic mRNA directed by a sequence derived from poliovirus RNA. Nature 334:320–325.
Pelletier, J., and N. Sonenberg. 1989. Internal binding of eucaryotic ribosomes on poliovirus RNA: translation in HeLa cell extracts. J. Virol. 63:441–444.
Rose, J. K., H. Trachsel, K. Leong, and D. Baltimore. 1978. Inhibition of translation by poliovirus: inactivation of a specific initiation factor, Proc. Natl. Acad. Sci. USA 75:2732–2736.
Sonenberg, N. 1990. Poliovirus translation. Curr Top Microbiol Immunol 161:23–47.
Trono. D., J. Pelletier, N. Sonenberg, and D. Baltimore. 1988. Translation in mammalian cells of a gene linked to the poliovirus 5' noncoding region. Science 241:445–448.

* cited by examiner

*Primary Examiner*—John L. LeGuyader
*Assistant Examiner*—Mark L. Shibuya
(74) *Attorney, Agent, or Firm*—Christensen O'Connor Johnson Kindness PLLC

(57) ABSTRACT

Retroviral vectors for producing coordinately expressed polycistronic mRNA in transfected host cells. A representative retroviral construct capable of forming a proviral genome in a host cell contains a first nucleotide coding sequence, a second nucleotide coding sequence, and a third nucleotide sequence capable of hybridizing under stringent conditions to a 5' nontranslated region (NTR) of a picornavirus RNA or its complementary RNA strand. The first, second, and third nucleotide sequences are operably linked such that transcription of the proviral genome gives rise to a messenger RNA molecule containing transcripts of the first, second, and third nucleotide sequences. The transcript of the third nucleotide sequence in the messenger RNA molecule contains a nucleic acid capable of forming a regulatory stem-loop nucleic acid structure followed by at least one operable AUG start codon. The regulatory stemloop nucleic acid structure is capable of operably binding a translation initiation complex in a host cell such that the transcripts of the first and second nucleotide sequences in the messenger RNA molecule are coordinately expressed in the host cell.

16 Claims, 2 Drawing Sheets

CAP-INDEPENDENT MULTICISTRONIC RETROVIRAL VECTORS

This application is a continuing application based on prior copending application Ser. No. 07/743,513, filed on Aug. 12, 1991, now abandoned.

This invention was made with government support under grants HL36444 and HLA41212 awarded by the Public Health Service and grants AI19565 and DK38531 awarded by the National Institutes of Health. The government has certain rights in the invention.

FIELD OF THE INVENTION

This invention relates to genetic engineering involving recombinant DNA technology, and particularly to retroviral vectors for producing coordinately expressed polycistronic mRNA in transfected host cells.

BACKGROUND OF THE INVENTION

Translation of typical eukaryotic mRNAs begins with the binding of initiation factors and the 40S small ribosomal subunit to the capped 5' end of an mRNA, followed by the migration of this complex to the first AUG codon in a suitable context for initiation of translation, where the complete ribosomal initiation complex is formed and protein synthesis begins. Picornavirus infection of cells causes a reduction in the translation of cellular RNA. In the case of poliovirus and several other members of the picornavirus family, the reduction is at the step of cap-dependent binding of ribosomal components to cellular mRNAs, and is due to inactivation of cap binding protein eIF-4F by a viral protease (25,26; see the appended Citations). Uncapped viral RNA continues to be translated in a cap-independent manner, and is dependent on the presence of unusually long 5' nontranslated regions (NTRs), ranging from 650 to 1300 nucleotides (nt), in the viral mRNA. These NTRs contain multiple AUG codons that appear not to initiate translation. In the case of poliovirus, mutation of 6 of the 7 upstream AUG codons had no effect on virus replication in cultured cells, and mutations in the seventh AUG only reduced the replication rate of the virus (20).

Several lines of evidence suggest that picornavirus NTRs provide sites for direct binding of ribosomes and thus allow internal initiation of protein translation from downstream AUG codons. First, although downstream coding regions in multicistronic RNAs are usually expressed poorly in mammalian cells or in in vitro mammalian translation systems, insertion of the 5' NTR from either poliovirus or encephalomyocarditis virus (EMCV) promotes efficient translation of downstream cistrons in in vitro and transient in vivo assays (3,4,22,28). Second, insertion of a 5' NTR upstream of a heterologous protein coding region renders translation of that cistron independent of poliovirus infection in cultured cells and in cellular extracts from infected and uninfected cells (3,21,22,28). Lastly, internal binding of ribosomes to 5' NTR regions has been demonstrated in vitro, and involves the binding of additional cellular but not viral proteins (5,8,23). A limitation of these experiments using plasmid vectors is the use of in vitro or transient in vivo assays for measurement of translation initiation. Furthermore, it was not apparent that such picornavirus 5' NTR systems could operate in a retroviral context.

A general limitation of prior retroviral vector techniques is that, if more than one gene (i.e., more than one cistron) is to be included in the retroviral construct, an internal promoter (e.g., an SV40 promoter) or mRNA alternative splicing may be required to obtain independent expression of the second gene. Otherwise (in the absence of splicing) transcription of the retroviral DNA will result in a polycistronic mRNA that encodes a polyprotein. Unfortunately, using multiple internal promoters or alternative splicing is only a partial solution to this problem and frequently leads to other difficulties because, for example, (a) each gene is independently expressed and selecting for one gene does not insure that expression of the other gene will be optimal; (b) the level of alternative splicing is highly variable in different types of cells; and (c) multiple promoters may interfere with one another. Although it is routine in the retroviral vector art to engineer such prior polycistronic vectors, many technical problems are commonly encountered. For example, selectable markers are routinely used to select transformed cells having integrated retroviral DNA, and while the growth of cells expressing high levels of the marker are favored, the selection of cells expressing the other gene, e.g., of therapeutic interest, may not be favored. It would therefore be highly desirable to be able to select simultaneously for expression of the marker gene and the gene of interest, but without encoding a polyprotein or relying on an alternatively spliced mRNA. Thus, it would be highly desirable to provide a retroviral construct in which the expression of two or more genes could be linked such that selection for optimal expression of one gene will ensure the coordinate expression of the other gene(s). For example, it would be desirable to be able to select simultaneously for expression of a selectable marker, a second gene of interest encoding a cytosolic protein, and a third gene of interest encoding a secreted protein.

SUMMARY OF THE INVENTION

To overcome the aforementioned limitations of the prior art, we have examined internal initiation from 5' NTRs by using bicistronic retroviral vectors for the generation of stable cell lines. We find that insertion of encephalomyocarditis virus (EMCV) or poliovirus 5' NTRs between the two coding regions markedly stimulates translation of the downstream cistron. Because both proteins are coordinately expressed from a single mRNA, this approach to the synthesis of multiple proteins by retroviral vectors has advantages over other methods that employ alternate splicing or internal promoters. Hence selection for expression of one of the genes should ensure expression of the other, which is not the case when using other strategies.

The invention provides, in one embodiment, retroviral constructs capable of forming a proviral genome in a host cell including a first nucleotide coding sequence, a second nucleotide coding sequence, and a third nucleotide sequence capable of hybridizing under stringent conditions to a 5' nontranslated region (NTR) of a picornavirus RNA or its complementary RNA strand. The first, second, and third nucleotide sequences are operably linked in the retroviral construct such that transcription of the proviral genome gives rise to a messenger RNA molecule containing transcripts of the first, second, and third nucleotide sequences. In a representative embodiment, one of the first and second nucleotide sequences encodes a detectable marker and the other of the nucleotide coding sequences encodes a therapeutic gene product. The retroviral construct will typically also contain retroviral elements for a 5' long terminal repeat sequence, a 3' long terminal repeat sequence having a poly-A tail, a psi-packaging signal, and a 5' segment of gag capable of promoting encapsidation of the retroviral construct into a retroviral vector particle.

Coordinate expression of the first and second coding sequence is ultimately achieved because the transcript of the third nucleotide sequence in the aforesaid messenger RNA molecule contains a nucleic acid capable of forming a regulatory stem-loop nucleic acid structure followed by at least one operable AUG start codon. This regulatory stem-loop nucleic acid structure is capable of operably binding a translation initiation complex in a host cell such that the transcripts of the first and second nucleotide sequences in the messenger RNA molecule are coordinately expressed in the host cell.

In a related embodiment, the invention provides packaging host cells transfected with the subject retroviral construct. The transfected cells are capable of encapsidating infective retroviral vector particles having a virion RNA complementary to the first, second, and third nucleotide sequences in the aforesaid proviral genome. Infective retroviral vector particles encapsidated by the packaging host cells are thereby provided.

In another related embodiment, the invention provides producer host cells transduced with the subject retroviral vector particles. The genome of the producer host cell contains a first proviral genome corresponding to the subject retroviral construct in combination with a second proviral genome containing a gag and pol gene and a third proviral genome containing an env gene. Such producer host cells are capable of encapsidating infective retroviral vector particles having a virion RNA complementary to the first, second, and third nucleotide sequences in the aforesaid first proviral genome. Infective retroviral vector particles produced by the producer host cell are thereby provided. Target host cells are transduced with these retroviral vector particles. The transduced target host cells contain the first proviral genome and are capable of expressing the gene products of the first and second nucleotide sequences. The first and second gene products expressed by the target host cells are thereby provided.

The subject producer host cells may alternatively be transfected with the subject retroviral construct. The genome of such transfected producer host cells contains a first proviral genome corresponding to the retroviral construct in combination with a second proviral genome containing a gag and pol gene and a third proviral genome containing an env gene. Such producer host cells are capable of encapsidating infective retroviral vector particles having a virion RNA complementary to the first, second, and third nucleotide sequences in the first proviral genome. Infective retroviral vector particles produced by these producer host cells are provided, as are target host cells transduced with these retroviral vector particles. Such target host cells contain the first proviral genome and are capable of expressing the gene products of the first and second nucleotide sequences. The first and second gene products expressed by these target host cells are thereby provided.

The subject target host cells may alternately be transfected with the subject retroviral constructs. Such target host cells contain the proviral genome and are capable of expressing the gene products of the first and second nucleotide sequences. This is another way of providing the first and/or second gene products.

DETAILED DESCRIPTION OF THE PREFERRED EMBODIMENT

Figure 1:
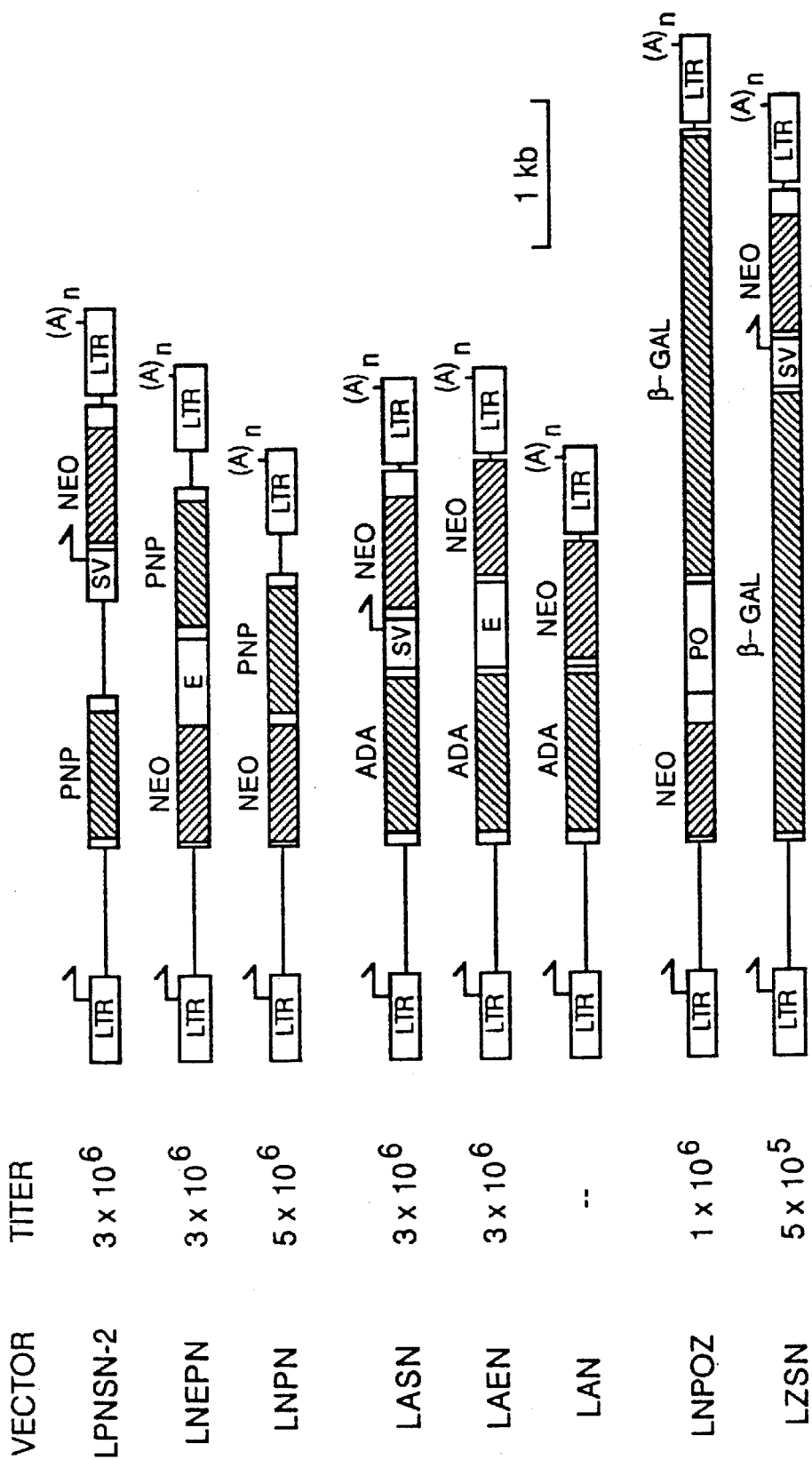
FIG. 1 depicts representative retroviral vectors as described in the working examples below.

Previous work has shown that picornavirus 5' nontranslated regions (NTRs) can initiate internal translation of downstream coding regions in plasmid systems, both in vitro and in transient in vivo assays. We have used 5' NTR sequences from encephalomyocarditis virus and poliovirus to construct retroviral vectors that are designed to express two (or more) proteins from a single mRNA. Inclusion of 5' NTR sequences did not adversely affect vector titer. Protein expression was studied in stable cell lines generated by vector infection of mouse NIH 3T3 cells and human and canine skin fibroblasts. Expression of a coding region in the downstream position was at levels from 25 to 100% of the same coding region in the upstream position. Expression of downstream coding regions in control vectors that did not contain the 5' NTR sequences was very low, in agreement with the predictions of the scanning model for eukaryotic translation. These experiments demonstrate coordinate expression of two coding regions from a single mRNA in stable cell lines, and provide further support for the model of internal translation initiation by sequences in the 5' NTRs of picornaviruses.

These results are surprising because it was unclear from the prior plasmid experiments whether the 5' NTR elements would be functionally preserved when incorporated into the context of a retroviral construct. Such retroviral constructs must generally undergo reverse transcription and integration into a host cell genome prior to expressing a functional transcript. It was uncertain whether the stem-loop nucleic acid structure (thought to be necessary for 5' NTR activity) could be successfully encoded by such an integrated retroviral proviral genome, as contrasted with its normal functional site in a picornavirus RNA in the cytoplasm of an infected cell. This was particularly an issue because it is known that retroviral reverse transcriptase has a relatively high error rate, and it had been suggested that even a single base change might be sufficient to inactivate the function of a 5' NTR in a wild-type picornavirus. It was also unclear whether a retroviral LTR would exert downstream promoter effects on the internal picornavirus 5' NTR, and, as well, whether the 5' NTR might interfere with retroviral integration or transcription. Furthermore, even if the 5' NTR could be expressed from a retroviral proviral genome, it might not regulate coordinate expression to a useful degree in transfected cells. In spite of these uncertainties, we found that the picornavirus 5' NTR is preserved during the retroviral life cycle, such that its transcript functions in a polycistronic messenger RNA transcribed from the retroviral proviral genome to mediate internal initiation of translation of the downstream cistron.

In describing the embodiments of the invention, the following terms are employed.

"Retroviral construct" is meant to encompass recombinant ribonucleic acid molecules having a nucleotide sequence homologous or complementary with a nucleotide sequence in an RNA retrovirus, or molecules capable of hybridizing thereto under stringent conditions.

"Retrovirus" means viruses having a virion RNA and utilizing reverse transcriptase for propagation of virus in a host cell.

"Host cell" encompasses mammalian and other cells that can be transfected or transduced by the subject retroviral vector constructs.

"5' NTR" means the 5' nontranslated region of a picornavirus ribonucleic acid capable of operably binding a translation initiation complex in a host cell.

"Proviral genome" refers to a recombinant deoxyribonucleic acid molecule having a nucleotide sequence homologous or complementary with a retroviral construct nucleotide sequence, or molecules capable of hybridizing under stringent conditions with same.

"Capable of hybridizing under stringent conditions" means annealing to a 5' nontranslated region (NTR) of a picornavirus RNA or its complementary strand under standard conditions, e.g., high temperature and/or low salt content, which tend to disfavor hybridization. A suitable protocol (involving 0.1×SSC, 68° C. for 2 hours) is described in Maniatis, T., et al., Molecular Cloning: A Laboratory Manual, Cold Spring Harbor Laboratory, 1982, at pages 387–389.

"Complementary strand" means a sequence of nucleotide bases which is capable of base-pairing (A to T or U, and G to C) with a single-stranded RNA or DNA molecule, and particularly to a 5' NTR sequence of a picornavirus RNA. The term as used herein permits some mismatching of bases in this pairing as long as the complementary strand is capable of hybridizing under stringent conditions with the single-stranded RNA or DNA molecule to form a double-stranded molecule.

"Operably linked" means nucleotide sequences which are linked in the proper reading frame, whether to encode an mRNA transcript of a desired gene product or for a desired regulatory control.

"Detectable marker" encompasses selectable markers and assay markers.

"Selectable markers" encompass a variety of gene products through which cells transformed with the retroviral construct can be selected or screened, including drug resistance markers, antigenic markers useful in fluorescence activated cell sorting, adherence markers such as receptors for adherence ligands allowing selective adherence, and the like.

"Assay markers" encompass a variety of gene products that can be detected in experimental assay protocols, such as marker enzymes, antigens, amino acid sequence markers, cellular phenotypic markers, nucleic acid sequence markers, and the like.

"Polypeptide" refers to a sequence of more than 3 amino acids linked together through peptide bonds. A representative list of polypeptides that are considered "therapeutic gene products" includes: therapeutic polypeptides; regulatory proteins such as those exerting their effects on gene expression; cytokines and interleukins and their receptors and inhibitors; hematological growth factors and their receptors and inhibitors; enzymes and their inhibitors; antigenic epitopes and their specific binding partners including antibodies; protease inhibitors and antiproteases; clotting factors and fibrinolytic factors; viral vaccines; and antiviral agents.

"Nucleotide sequence" indicates a sequence of linked purine and pyrimidine bases.

"Regulatory gene" refers to a nucleotide sequence which when placed adjacent a second nucleotide sequence will alter the expression of the second sequence.

"Expression" and "gene expression" are interchangeably used herein to indicate transcription and/or translation of a nucleotide sequence in a cell, creating a ribonucleic acid or polypeptide gene product, respectively.

"Regulatory stem loop nucleic acid structure" as used herein refers to ribonucleic acid structures capable of binding a translation initiation complex in a cell and initiating internal translation of a nucleic acid in the cell.

"Operable AUG start codon" refers to an AUG, carried by the 5' NTR or downstream cistron, which is capable of initiating translation of the downstream nucleotide sequence in a reading frame suitable for obtaining the amino acid sequence of the encoded polypeptide.

"Operably binding a translation initiation complex" in a cell means binding of a translation initiation complex to the 5' NTR such that a nucleotide sequence placed downstream from the 5' NTR will be translated in a reading frame suitable for obtaining the amino acid sequence of the encoded polypeptide.

"Coordinately expressed" means transcription and translation of two or more nucleotide sequences in a polycistronic mRNA.

The invention provides, in one embodiment, polycistronic retroviral vector constructs for coordinately expressing two or more genes from a single messenger RNA molecule. The subject retroviral constructs are capable of forming a proviral genome in a host cell that encodes a polycistronic mRNA that is translated into more than one gene product, i.e., not into a polyprotein. For example, coordinate expression of a selectable marker gene and a therapeutic gene of interest is accomplished by operably linking the marker gene and the gene of interest to a nucleotide sequence capable of hybridizing under stringent conditions to a 5' nontranslated region (NTR) of a picornavirus RNA or its complementary RNA strand.

Suitable 5' NTRs for this purpose include picornavirus 5' NTRs that are identified by methods known in the art or as described herein. Such 5' NTR sequences are generally identified by their ability to direct internal initiation of translation in a polycistronic mRNA. It is contemplated that new virus, viral variants and strains, and genetically engineered virus may be identified and prepared containing modified picornavirus or other (e.g., mammalian) 5' NTR sequences that are structurally related to the native 5' NTR stem-loop nucleic acid structure, and/or that hybridize with the 5' NTR sequences of known picornaviruses. Standard techniques known in the art can be used to engineer, select, and identify modified 5' NTRs which have increased (or decreased) binding affinity for a particular differentiation-stage-specific translation initiation complex, e.g., in de-differentiated carcinoma or melanoma cells having stage specific translation initiation complexes.

The subject retroviral constructs preferably contain a nucleotide sequence that encodes a detectable marker to facilitate identification of host cells transformed by the retroviral construct and expressing the gene products encoded by the retroviral construct. The detectable marker may be a drug resistance marker (e.g., neo, encoding neomycin phosphotransferase; hprt, hypoxanthine phosphoribosyltransferase; his, histindinol dehydrogenase; hygro, hygromycin; pur, puromycin; dhfr, dihydrofolate reductase; tk, thymidine kinase; ada, adenosine deaminase; amp, ampicillin; tet, tetracycline), in which case the transformed host cell can be selected by adding the drug to cultures of cells transfected or transduced with the retroviral vector construct. Since the gene of interest is coordinately linked in the retroviral mRNA with the selectable marker, it is only necessary to identify cells with high level expression of transcripts for the detectable marker to also identify cells with high level expression of the gene of interest.

Where the detectable marker employed in the retroviral construct is a translation product that serves as an assay marker (e.g., marker enzymes, marker antigens, amino acid sequence markers, cellular phenotypic markers, etc.), screening of cells for high level expression of the assay marker may involve increased translational efficiency of the marker transcripts, higher level of transcripts, and/or longer half life of the transcripts. This may be accomplished by routine nucleic acid methods, or by assaying for a functional activity related to expression of the gene of interest.

The retroviral constructs are preferably rendered replication defective, by methods routine in the art, and contain at least a psi-packaging signal, a 5' segment of gag (or mutated gag) capable of promoting encapsidation of the retroviral construct into a retroviral vector particle, portions of a U3 or U5 sequence sufficient for retroviral integration into a host cell, and a polyA tail to promote translation. Such replication defective retroviral vector constructs are preferably packaged in a packaging host cell, such as PA317, having requisite portions of the gag nucleotide sequences for forming a viral core, the env sequence for encapsidating the virion particle, and pol sequences encoding reverse transcriptase. Such packaging host cells transfected with the retroviral construct are capable of forming a ribonucleoprotein core particle containing the retroviral construct and of encapsidating the core with a membrane such that infective retroviral vector particles are produced that have the virion of the defective (i.e., replication incompetent) retroviral construct. The packaging cells may be transfected and selected to obtain a cell line containing the integrated retroviral construct as a proviral genome, or the cells may be used in a transient transfection assay, i.e., to produce a source of retroviral vectors for use in infecting a second host cell line.

The invention also provides producer host cells transduced with the retroviral vector particles, such as from a transiently transfected packaging cell line, or by transfection with the retroviral construct. These producer host cells can be selected for functional properties, e.g., high titer virus production or increased safety for use in a particular mammalian host. To effectively encapsidate the transcripts from the proviral genome of the retroviral construct, these cells minimally need to have packaging and encapsidation functions such as those discussed above for the packaging cells. A split retroviral genome is preferably employed in the producer cell, e.g., portions of a gag and pol gene in one proviral genome and of an env gene in another proviral genome.

Infective retroviral vector particles produced by either the packaging or producer host cell are useful to infect cells in a mammalian host, e.g., by injecting the defective retroviral vector into the mammalian host. Alternatively, cells of the mammalian host can be transduced in vitro and then returned to the host. In the latter case the target host cell may be transduced with the retroviral vector particles, and the cells selected and/or tested for expression of the gene of interest, etc., prior to returning the genetically engineered cells to the mammalian host.

It is also recognized that the producer cells of the invention are useful for expressing the gene product of interest in cell culture, e.g., for manufacturing recombinantly-derived polypeptides.

EXAMPLES

In the representative examples that follow, we have demonstrated stable expression of both adenosine deaminase (ADA) and purine nucleoside phosphorylase (PNP) genes in bicistronic mRNAs transcribed from retroviral vectors in which encephalomyocarditis virus (EMCV) or poliovirus 5' NTR sequences have been inserted between the two coding regions. Analysis of RNA from infected cells reveals only full-length genomic messages, and no subgenomic spliced or internally initiated mRNAs that could account for expression of the downstream coding region. The level of PNP expression in such bicistronic mRNAs was similar when PNP was in the upstream or downstream position. Expression of neo in the downstream position was 25 to 50% of that observed when neo was in the upstream position. These results provide strong evidence for internal initiation of translation in mammalian cells, and document a mode of translation in stable cell lines that is distinct from the scanning model for translation (6).

In the vectors described here, the poliovirus 5' NTR sequences were truncated before the natural poliovirus start codon, while the EMCV 5' NTR sequences still contain the natural EMCV start codon. This start codon is out of frame with the downstream coding regions in the LNEPN and LAEN vectors. In LNEPN, the EMCV start codon is followed 2 codons downstream by a stop codon, and we presume that such a short open reading frame does not interfere with translation initiation at the downstream start codon of PNP. In the LAEN vector, the EMCV start codon is followed 21 codons downstream by a stop codon which overlaps the start codon of neo. That we find relatively efficient translation of the downstream neo coding region in the LAEN vector is consistent with previous results showing that a coding region that lies downstream of an open reading frame can be efficiently translated when the start codon of the downstream coding region is close to the stop codon of the upstream open reading frame (7,18,19,27). Presumably, under these conditions the ribosomal complex reinitiates translation at the nearby start codon before the components have had time to dissociate. It is still possible, however, that elimination of the EMCV start codon or an in-frame fusion of the downstream coding region with this start codon might increase expression of the downstream coding regions in these vectors.

Insertion of the 5' NTRs from EMCV or poliovirus into several retroviral vectors did not interfere with the production of high-titer virus from the vectors. It is tempting to speculate that retroviral vectors containing a string of coding regions separated by 5' NTRs could be designed to allow coordinate expression of multiple cDNAs. Such constructions would be limited by size constraints on retroviral vectors, around 7 to 10 kb, and the potential for recombination between identical 5' NTRs resulting in cDNA deletion.

Cells infected with vectors containing ADA linked to the viral LTR, LASN and LAEN, produced from 4- to 30-fold higher ADA activities than the PNP activities produced by cells infected with the corresponding PNP-vector LPNSN-2. This difference is not due to increased protein synthesis from the ADA-vectors, but is due to the 10-fold higher specific activity of the ADA protein compared with PNP (14,15).

Although expression of the two coding regions in vector containing 5' NTRs is linked at the transcriptional level by their presence on the same RNA, there are conditions that can alter the ratio of translation by cap-directed or internally-initiated mechanisms. Poliovirus infection of cells drastically reduces the rate of cap-dependent translation while internally-initiated translation is greatly increased due to facilitated access to the translational machinery (26). It will be interesting to see if there are conditions in normal cells that influence the ratio of translation by these two mechanisms. The use of retroviral vectors for the promotion of unrearranged, single-copy insertions of these bicistronic genes will facilitate these studies.

Materials and Methods

Cell Culture. PA317 amphotropic retrovirus packaging cells (10, American Type Culture Collection #CRL 9078), PE501 ecotropic retrovirus packaging cells (12), and NIH 3T3 TK-cells (10) were grown in Dulbecco modified Eagle medium with high glucose (4.5 g/l) supplemented with 10% fetal bovine serum (Hyclone, Logan, Utah). Human and canine diploid fibroblasts were cultured in Waymouth medium and were isolated from skin biopsies of normal human and canine donors and from adenosine deaminase (ADA) deficient and purine nucleoside phosphorylase (PNP) deficient patients.

Retroviral Vector Construction. Scale drawings of the retroviral vectors are shown in FIG. 1. Vector descriptions are based on the order of sequence elements within the vector, including promoters, coding regions, and viral translation initiation sites.ABbreviations and symbols are as follows: LTR, retroviral long terminal repeat; SV, simian virus 40 early promoter and enhancers; E, EMCV 5' nontranslated region; PO, poliovirus 5' nontranslated region; PNP, human purine nucleoside phosphorylase cDNA; NEO, bacterial neomycin phosphotransferase cDNA; ADA, human adenosine deaminase cDNA; β-GAL, β-galactosidase cDNA with synthetic mammalian translation start codon; (A)$_n$, polyadenylation signal; kb, kilobases. Hatched areas indicate protein coding regions, lines indicate viral sequences other than the LTR sequences, including the extended virus packaging signal (1) that follows the retroviral LTR. Vector names are based on the order of genetic elements within the vector: L, LTR; PN, PNP; S, SV40 promoter; N, NEO; A, ADA; E, EMCV 5' sequences; PO, poliovirus 5' sequences; Z, LacZ gene or β-gal. Plasmid forms of retroviral vectors are preceded by "p" while the viral form has no prefix. We thank Sung K. Jang for the pBS-ECAT plasmid that contains the EMCV 5' nontranslated region, and Nahum Sonenberg for the pP2-5' plasmid that contains the poliovirus 5' nontranslated region.

Construction of pLPNSN-2 has been described (15). Plasmid pLNPN was made from pLNSPN (15) by deletion of the SV40 promoter. Plasmid pLNEPN was made from pLNSPN (15) by replacement of the SV40 promoter with the EMCV 5' nontranslated region from base 260 to 837 obtained as an EcoRI to BalI fragment from pBS-ECAT (3). This segment contains the internal ribosomal entry site and sequences that augment efficient initiation of translation (5). Plasmid pLASN has been described (2). Plasmid pLAN was made by insertion of the ADA coding region from pLASN into pLXSN (12) in place of the SV40 promoter. Plasmid pLAEN was made by insertion of the EMCV fragment described above between the neo and ADA genes of pLAN. Plasmid pLNPOZ was made by replacing the SV40 sequences in pLNSX (12) with the 5' nontranslated sequences from base 1 to 732 of poliovirus type 2 (Lansing) obtained as a HindIII to EcoRV fragment from pP2-5' (21) followed by β-galactosidase (β-gal) sequences isolated from pLacD (kind gift from Jacques Peschon and Richard Palmiter, University of Washington, Seattle, Wash.). pLacD contains a synthetic translation initiation codon and proper surrounding sequences (ACC<u>ATG</u>G; 6) for efficient translation of the bacterial β-gal gene in mammalian cells. pLZSN (K. Burck and A. D. Miller, unpublished data) was made by inserting a BglII fragment containing the β-gal coding region from pLacD into the BamHI site of pLXSN (12).

The plasmid designated LNEPN was deposited on Aug. 9, 1991, under accession No. 75056 at the American Type Culture Collection, 12301 Parklawn Drive, Rockville, Md.

Virus Production and Assay. Virus was generated from the vector plasmids as previously described (12,13). Briefly, plasmids were introduced into PE501 cells by calcium phosphate-mediated transfection and virus was harvested two days later and used to infect PA317 cells. Clonal PA317 cell lines were isolated following selection of the infected cells in 0.75 mg/ml G418 (actual concentration). About 10 infected PA317 clones for each vector were screened for high titer virus production by assay of secreted virus on NIH 3T3 TK$^-$ cells. Clonal PA317 cell lines were isolated that produced from $5 \times 10^5$ to $5 \times 10^6$ G418-resistant colony forming units (cfu)/ml of medium harvested from the cells for all of the vector except LAN (see below).

Enzyme Assays. Activities of adenosine deaminase (ADA) and purine nucleoside phosphorylase (PNP) were determined by spectrophotometric assays using adenosine and inosine, respectively, as substrates (14,16). Relative amounts of human, mouse, and dog ADA or PNP in cell extracts was determined by starch gel electrophoresis (16), which separates the enzymes from different species. Neomycin phosphotransferase activity (NPT) was determined as described (24) by measuring $^{32}$P-ATP phosphate transfer to neomycin by cell extracts. Nonspecifically labelled protein was removed by phenol/chloroform extraction of the reaction mixture prior to product adsorption to DEAE anion exchange paper and quantitation by scintillation counting.

Example 1

Retroviral Vector Construction and Virus Production

Retroviral vector construction and virus production. The retroviral vectors used here are all derivatives of the Moloney murine leukemia virus (MoMLV)-based vector LNL6 (1). The viral sequences surrounding the inserted genes are identical, and include the extended packaging signal required for high-titer virus production (1). This signal includes a portion of the gag gene of MoMLV, but the start codon has been changed to TAG to prevent gag translation, and to provide efficient translation of downstream sequences (12).

Included in the vectors are cDNAs encoding human adenosine deaminase (ADA), human purine nucleoside phosphorylase (PNP), and bacterial neomycin phosphotransferase (NPT), all of which can be quantitated by enzymatic assays. Referring to FIG. 1, EMCV (E) and poliovirus (PO) 5' NTRs have been inserted between the cDNAs in LNEPN, LAEN, and LNPOZ to study their effects on downstream translation. The sequences separating the coding regions in these vectors are from 677 to 1001 bp long and contain from 11 to 13 ATGs. The vectors LNPN and LAN serve as controls for expression of downstream coding regions in bicistronic mRNAs. Approximately 100 bp separate the coding regions in these vectors, and there are no intervening ATGs in LNPN and only 2 ATGs in nonoptimal contexts for initiation of translation (6) in LAN. Additional controls involve the insertion of an SV40 early promoter and enhancers between the coding regions to promote translation of the second coding region from an SV40-initiated subgenomic mRNA.

Amphotropic helper-free virus was made from the plasmid forms of the vectors by using PA317 retrovirus packaging cells (9,10), as previously described (see Materials and Methods). G418-resistant PA317 clones that contained single unrearranged proviruses were chosen for study. Virus with titers from $5 \times 10^5$ to $5 \times 10^6$ colony-forming units (cfu)/ml were obtained from all of the constructs except pLAN, where 6 of 6 G418-resistant clones examined contained rearranged proviruses by Southern analysis. The rearrangements involved partial or complete deletion of ADA sequences, and we conclude that neo expression from the downstream coding region in this bicistronic vector was not sufficient to confer G418 resistance to the PA317 cells without the deletion of ADA sequences.

When compared to results for the parent vectors, the inclusion of 5' NTR sequences from EMCV or poliovirus did not significantly alter the vector titer. For example, the three vectors LPNSN-2, LNEPN, and LNPN all contain neo and PNP coding regions and either an SV40 promoter, 5' NTR, or no additional sequence, and all had titers from 3 to $5\times10^6$ cfu/ml. Similarly, LASN and LAEN, which both contain neo and ADA coding regions, had the same titers. LNPOZ and LZSN, which both contain neo and β-gal coding regions, had similar titers, which are somewhat lower than the other vectors, probably due to the presence of the β-gal coding region.

Example 2

Analysis of Enzyme Activities in Vector-infected PA317 Cells

Vector producing cells infected with the PNP-vectors LPNSN-2, LNEPN, and LNPN were assayed for ADA, PNP, and NPT activities. Results are shown in Table 1.

TABLE 1

Enzyme levels in vector-infected PA317 cells.

| Virus | ADA | PNP | NPT |
|---|---|---|---|
| None | 1.8 | 2.1 | <2 |
| LPNSN-2 | 1.8 | 6.8 | 48 |
| LNEPN | 1.9 | 6.7 | 320 |
| LNPN | 1.2 | 1.6 | 170 |
| LASN | 16.2 | 2.0 | 60 |
| LAEN | 19.4 | 2.1 | 120 |
| LNPOZ | 1.8 | 1.4 | 330 |

ADA and PNP activities are μmol/hr/mg protein. The mean coefficient of variation of these assays was 5%.
NPT activity is pmol/hr/mg protein, and the results from duplicate determinations varied by no more than 10%.

Insertion of the EMCV 5' NTR between neo and the PNP coding region in LNEPN resulted in a 3-fold increase in PNP activity in PA317 cells infected with this vector compared to uninfected cells. A similar increase in PNP activity was seen in cells infected with the LPNSN-2 vector, where PNP is the first coding region after the viral LTR. Starch gel analysis showed that the PNP activity in uninfected PA317 mouse cells was due to mouse PNP, while the increases observed in the vector-infected cells were due to human PNP (data not shown). Positioning PNP downstream of neo in LNPN resulted in PNP activity equivalent to levels found in cells not infected with a PNP vector. ADA activities in the PNP-vector-infected PA317 cells were similar to uninfected control cells. Thus, positioning the EMCV 5' NTR between two coding regions in a single transcriptional unit elevates expression of the downstream coding region to levels obtained when the coding region is in the upstream position.

ADA, PNP, and NPT activities were also measured in PA317 cells infected with the vectors carrying neo. Positioning neo as the first coding region following the LTR in LNEPN, LNPN, and LNPOZ resulted in an average of 270 units of NPT activity. When neo was positioned downstream of the ADA coding region in the LAN vector, G418-resistant PA317 clones containing an unrearranged provirus were not obtained, suggesting poor neo expression by the LAN vector. In contrast, when the EMCV 5' NTR was inserted between ADA and neo in LAEN, PA317 cells infected with this vector expressed 120 units of NPT activity, or about half of the activity seen when neo was positioned near the LTR. PA317 cells infected with LAEN made about 10-fold higher levels of ADA than cells not infected with an ADA vector, and the increase in ADA was shown to be due to human enzyme by starch gel analysis (data not shown); thus the ADA coding region in LAEN was functional. Expression of neo from an internal SV40 promoter in LASN or LPNSN-2 resulted in 60 units of NPT activity. This is in agreement with our previous results showing the viral LTR to be a stronger promoter than SV40 (2,15,17). These data confirm that inserting the EMCV 5' NTR between two coding regions in a single transcriptional unit results in translation of the downstream coding region at a rate approaching that of the upstream coding region.

Example 3

Analysis of Vector Expression in PNP-Human Fibroblasts

Human skin fibroblasts from a patient with PNP deficiency were infected with the three PNP-vectors, selected in G418, and enzyme activities were determined. Results are shown in Table 2.

TABLE 2

Enzyme levels in vector-infected PNP- human diploid fibroblasts.

| Virus | PNP | NPT |
|---|---|---|
| None | <0.01 | <2 |
| LPNSN-2 | 5.49 | 120 |
| LNEPN | 4.50 | 260 |
| LNPN | 0.10 | 180 |
| Normal | 0.74 | n.d. |

Units as in Table 1;
n.d., not done.

Figure 2:
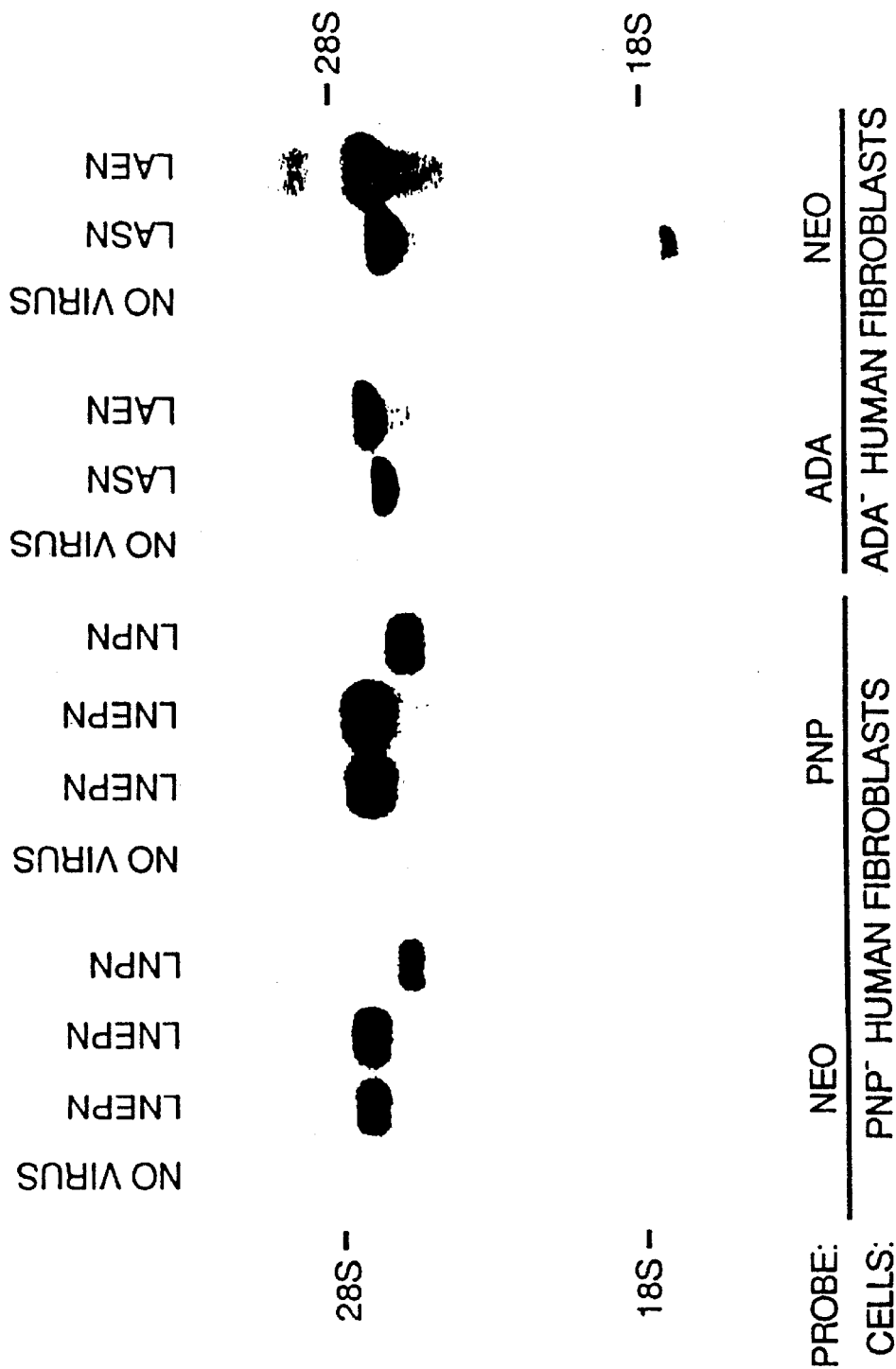
FIG. 2 presents representative data confirming coordinate expression of polycistronic mRNA in transfected host cells, as described below in Example 3.

Uninfected cells had undetectable PNP activity. PNP⁻ fibroblasts infected with LPNSN-2 or LNEPN vectors expressed PNP at about 8 times the level found in uninfected normal human fibroblasts. PNP activity could be detected in LNPN-infected cells, but was only about 15% of that found in uninfected normal human skin fibroblasts ("Normal"). NPT activities in the vector-infected cells were similar to those found in PA317 cells infected with the same vectors (Table 1). Analysis of RNA from the human PNP⁻ fibroblasts infected with LNEPN or LNPN vectors by using either a neo or a PNP probe confirmed the existence of single genome-length mRNAs of the expected sizes transcribed from each vector, and ruled out the possibility that spliced or internally promoted mRNAs were responsible for expression of the downstream PNP cDNA in these vectors. FIG. 2 shows this analysis of RNA from infected human fibroblasts. Total RNA was prepared from cells infected with the indicated vectors and selected in G418 or from cells that were not infected or selected. RNA was subjected to electrophoresis in denaturing formaldehyde gels, transferred to nylon membrane and hybridized with the indicated radiolabeled probes. 28S (4.5 kb) and 18S (1.8 kb) ribosomal markers are indicated. The sizes of the expected mRNAs from the different vectors, assuming 150 bp polyA at the 3' ends, are: LNEPN, 4.4 kb; LNPN, 3.8 kb; LASN, 4.3 and 1.7 kb; and LAEN, 4.4 kb. Thus, although there was some expression of PNP as the second gene in a bicistronic mRNA lacking any special sequences between the coding regions, expression of PNP was increased about 50-fold by inclusion of the EMCV 5' NTR between the coding regions.

Example 4

Analysis of Vector Expression in ADA-Human Fibroblasts

Human skin fibroblasts from a patient with ADA deficiency were infected with the LASN and LAEN vectors, selected in G418, and enzyme activities were determined. Results are shown in Table 3.

TABLE 3

Enzyme levels in vector-infected ADA- human diploid fibroblasts.

| Virus | ADA | NPT |
|---|---|---|
| None | <0.01 | <2 |
| LASN | 69 | 100 |
| LAEN | 169 | 60 |
| Normal | 0.9 | n.d. |

Units as in Table 1;
n.d., not done.

Both of the vectors expressed ADA at very high levels, up to 190-fold higher than uninfected normal human skin fibroblasts ("Normal"). Cells infected with LAEN expressed 60 units of NPT activity, which is 60% of the NPT level in cells infected with LASN, where neo is driven by an internal SV40 promoter, or about 25% of the NPT levels seen in the PNP⁻ human fibroblasts infected with LNEPN or LNPN, where neo is driven by the viral LTR (Table 2). Analysis of RNA from the human ADA⁻ fibroblasts infected with LASN or LAEN vectors by using either a neo or an ADA probe confirmed the existence of single genome-length mRNA of the expected sizes transcribed from each vector, and a smaller mRNA in LASN-infected cells that hybridized only to the neo probe and that had the size expected of an SV40-promoted subgenomic mRNA (FIG. 2). Thus the insertion of the EMCV 5' NTR between ADA and neo coding regions in a bicistronic mRNA promotes expression of the downstream neo coding region at a level approaching that directed by an internal SV40 promoter, and at 4-fold lower levels than that directed by the viral LTR.

Example 5

Analysis of Vector Expression in Canine Skin Fibroblasts

Normal dog skin fibroblasts were infected with the LASN and LAEN vectors, selected in G418, and analyzed for enzyme activities. Results are shown in TABLE 4.

TABLE 4

Enzyme levels in vector-infected dog skin fibroblasts.

| Virus | ADA | PNP | NPT |
|---|---|---|---|
| None | 0.9 | 0.94 | <2 |
| LASN | 26 | 0.69 | 57 |
| LAEN | 44 | 0.61 | 140 |

Units as in Table 1.

In both LASN- and LAEN-infected cells, ADA activities of 30- to 40-fold greater than in uninfected cells were observed. The PNP levels were similar in infected and uninfected cells. The NPT activity of LAEN infectants was about 2.5 times higher than that of cells infected with the LASN vector. This is similar to the results seen in PA317 cells where LAEN-infected cells produced 2-fold higher NPT activity than LASN-infected cells (Table 1). In contrast, the SV40 promoter provided about 2-fold higher levels of NPT activity than the EMCV 5' NTR in human skin fibroblasts (Table 3). Thus, on average, the EMCV 5' NTR enabled about the same levels of neo expression in a downstream position as the SV40 promoter.

Example 6

Use of the Poliovirus 5' NTR

We have also constructed a vector, LNPOZ (FIG. 1), with an internal poliovirus 5' NTR and upstream neo and downstream β-gal cDNAs. While we have not characterized LNPOZ as completely as the vectors containing the EMCV 5' NTR, LNPOZ provides similar levels of β-gal in infected cells, as judged by blue staining after incubation with X-gal, as the LZSN vector, in which β-gal is driven directly by the viral LTR (data not shown).

Example 7

Tricistronic Retroviral Constructs

Polycistronic retroviral vector LAPOZEN has also been constructed. The LAPOZEN vector contains the following sequence of elements: the aforesaid retroviral long terminal repeat (LTR); the human adenosine deaminase cDNA (ADA); the poliovirus 5' NTR (PO); the β-galactosidase cDNA with synthetic mammalian start codon (β-GAL); the EMCV 5' NTR (E); and the bacterial neomycin phosphotransferase cDNA (NEO). Thus, coordinate expression of β-GAL and NEO with that of the LTR-driven ADA cistron is provided by virtue of the internal PO and E 5' NTR sequences.

Citations

1. Bender, M. A., T. D. Palmer, R. E. Gelinas, and A. D. Miller. 1987. Evidence that the packaging signal of Moloney murine leukemia virus extends into the gag region. J. Virol. 61:1639–1646.
2. Hock, R. A., A. D. Miller, and W. R. A. Osborne 1989. Expression of human adenosine deaminase from various strong promoters after gene transfer into human hematopoietic cell lines. Blood 74:876–881.
3. Jang, S. K., M. V. Davies, R. J. Kaufman, and E. Wimmer. 1989. Initiation of protein synthesis by internal entry of ribosomes into the 5' nontranslated region of encephalomyocarditis virus RNA in vivo. J. Virol. 63:1651–1660.
4. Jang, S. K., H. G. Kräusslich, M. J. Nicklin, G. M. Duke, A. C. Palmenberg, and E. Wimmer. 1988. A segment of the 5' nontranslated region of encephalomyocarditis virus RNA directs internal entry of ribosomes during in vitro translation. J. Virol. 62:2636–2643.
5. Jang, S. K., and E. Wimmer. 1990. Cap-independent translation of encephalomyocarditis virus RNA: structural elements of the internal ribosomal entry site and involvement of a cellular 57-kD RNA-binding protein. Genes Dev. 4:1560–1572.
6. Kozak, M. 1989. The scanning model for translation: an update. J. Cell Biol. 108:229–241.
7. Liu, C.-C., C. C. Simonsen, and A. D. Levinson. 1984. Initiation of translation at internal AUG codons in mammalian cells. Nature 309:82–85.
8. Meerovitch, K., J. Pelletier, and N. Sonenberg. 1989. A cellular protein that binds to the 5' -noncoding region of poliovirus RNA: implications for internal translation initiation. Genes Dev. 3:1026–1034.

9. Miller, A. D. 1990. Retrovirus packaging cells. Human Gene Therapy 1:5–14.
10. Miller, A. D., and C. Buttimore. 1986. Redesign of retrovirus packaging cell lines to avoid recombination leading to helper virus production. Mol. Cell. Biol. 6:2895–2902.
11. Miller, A. D., M. F. Law, and I. M. Verma. 1985. Generation of helper-free amphotropic retroviruses that transduce a dominant-acting methotrexate-resistant DHFR gene. Mol. Cell. Biol. 5:431–437.
12. Miller, A. D., and G. J. Rosman. 1989. Improved retroviral vectors for gene transfer and expression. Bio-Techniques 7:980–990.
13. Miller, A. D., D. R. Trauber, and C. Buttimore. 1986. Factors involved in the production of helper virus-free retrovirus vectors. Somat. Cell Mol. Genet. 12:175–183.
14. Osborne, W. R. A. 1980. Human red cell purine nucleoside phosphorylase: Purification by biospecific affinity chromatography and physical properties. J. Biol. Chem. 255:7089–7092.
15. Osborne, W. R. A., and A. D. Miller. 1988. Design of vectors for efficient expression of human purine nucleoside phosphorylase in skin fibroblasts from enzyme-deficient humans. Proc. Natl. Acad. Sci. USA 85:6851–6855.
16. Osborne, W. R. A., and N. Spencer. 1973. Partial purification and properties of the common inherited forms of adenosine deaminase from human erythrocytes. Biochem. J. 133:117–123.
17. Palmer, T. D., A. R. Thompson, and A. D. Miller. 1989. Production of human factor IX in animals by genetically modified skin fibroblasts: potential therapy for hemophilia B. Blood 73:438–445.
18. Peabody, D. S., and P Berg. 1986. Termination-reinitiation occurs in the translation of mammalian cell mRNAs. Mol. Cell. Biol. 6:2695–2703.
19. Peabody, D. S., S. Subramani, and P. Berg. 1986. Effect of upstream reading frames on translation efficiency in simian virus 40 recombinants. Mol. Cell. Biol. 6:2704–2711.
20. Pelletier, J., M. E. Flynn, G. Kaplan, V. Racaniello, and N. Sonenberg. 1988. Mutational analysis of upstream AUG codons of poliovirus RNA. J. Virol. 62:4486–4492.
21. Pelletier, J., G. Kaplan, V. R. Racaniello, and N. Sonenberg. 1988. Cap-independent translation of poliovirus mRNA is conferred by sequence elements within the 5' noncoding region. Mol. Cell. Biol. 8:1103–1112.
22. Pelletier, J., and N. Sonenberg. 1988. Internal initiation of translation of eukaryotic mRNA directed by a sequence derived from poliovirus RNA. Nature 334:320–325.
23. Pelletier, J., and N. Sonenberg. 1989. Internal binding of eucaryotic ribosomes on poliovirus RNA: translation in Hela cell extracts. J. Virol. 63:441–444.
24. Ramesh, N. and W. R. A. Osborne. 1991. Assay of neomycin phosphotransferase activity in cell extracts. Anal. Biochem., in press.
25. Rose, J. K., H. Trachsel, K. Leong, and D. Baltimore. 1978. Inhibition of translation by poliovirus: inactivation of a specific initiation factor. Proc. Natl. Acad. Sci. USA 75:2732–2736.
26. Sonenberg, N. 1990. Poliovirus translation. Curr Top Microbiol Immunol 161:23–47.
27. Thomas, K. R., and M. R. Capecchi. 1986. Introduction of homologous DNA sequences into mammalian cells induces mutations in the cognate gene. Nature 324:34–38.
28. Trono, D., J. Pelletier, N. Sonenberg, and D. Baltimore. 1988. Translation in mammalian cells of a gene linked to the poliovirus 5' noncoding region. Science 241:445–448.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A retroviral construct capable of forming a proviral genome in a host cell, said retroviral construct comprising:
   a first nucleotide sequence comprising a MoMLV LTR,
   a second nucleotide sequence comprising a first coding region,
   a third nucleotide sequence, comprising a picornavirus NTR, wherein the picornavirus is selected from among encephalomyocarditis virus and poliovirus,
   a fourth nucleotide sequence comprising a second coding region, and
   a fifth nucleotide sequence comprising a poly-A tail,
   wherein said nucleotide sequences are operably linked such that transcription of the proviral genome gives rise to a messenger RNA molecule comprising transcripts of the second, third, fourth, and fifth nucleotide sequences.

2. The retroviral construct of claim 1, wherein one of said first and second coding regions encodes a detectable marker.

3. The retroviral construct of claim 2, wherein the other of said first and second coding regions encodes a therapeutic gene product.

4. The retroviral construct of claim 1, comprising MoMLV retroviral elements for packaging and encapsidation of the retroviral RNA into a retroviral vector particle.

5. The retroviral construct of claim 1, wherein the transcript of the third nucleotide sequence in said messenger RNA molecule comprises a nucleic acid capable of forming a regulatory stem-loop nucleic acid structure followed by at least one operable AUG start codon.

6. The retroviral construct of claim 5, wherein the regulatory stem-loop nucleic acid structure is capable of operably binding a translation initiation complex in a host cell such that the transcripts of the second and fourth nucleotide sequences in said messenger RNA molecule are coordinately expressed in the host cell.

7. A packaging host cell transformed with the retroviral construct of claim 1, capable of encapsidating infective retroviral vector particles having a virion RNA complementary to said nucleotide sequences in said proviral genome.

8. An infective retroviral vector particle encapsidated by the transformed packaging host cell of claim 7.

9. A producer host cell transduced with the retroviral vector particle of claim 8, the genome of said producer host cell comprising a first proviral genome corresponding to said retroviral construct in combination with a second proviral genome comprising a gag and pol gene and a third proviral genome comprising an env gene, said producer host cell being capable of encapsidating infective retroviral vector particles having a virion RNA complementary to said nucleotide sequences in said first proviral genome.

10. An infective retroviral vector particle produced by the producer host cell of claim 9.

11. A target host cell transduced with the retroviral vector particle of claim 10, said target host cell containing said first proviral genome and being capable of expressing the gene products of said second and fourth nucleotide sequences.

12. A producer host cell transformed with the retroviral construct of claim 1, the genome of said producer host cell comprising a first proviral genome corresponding to said retroviral construct in combination with a second proviral genome comprising a gag and pol gene and a third proviral genome comprising an env gene, said producer host cell being capable of encapsidating infective retroviral vector particles having a virion RNA complementary to said nucleotide sequences in said first proviral genome.

13. An infective retroviral vector particle produced by the producer host cell of claim 12.

14. A target host cell transduced with the retroviral vector particle of claim 13, said target host cell containing said first proviral genome and being capable of expressing the gene products of said second and fourth nucleotide sequences.

15. A target host cell transformed with the retroviral construct of claim 1, said target host cell containing said proviral genome and being capable of expressing the gene products of said second and fourth nucleotide sequences.

16. A retroviral construct capable of forming a proviral genome in a host cell said retroviral construct comprising:

a first nucleotide sequence comprising a MoMLV LTR a second nucleotide sequence comprising a first coding region, a third nucleotide sequence comprising a picornavirus NTR, wherein the picornavirus is selected from among encephalomyocarditis virus and poliovirus, a fourth nucleotide sequence comprising a second coding region, a fifth nucleotide sequence comprising a picornavirus NTR, wherein the picornavirus is selected from among encephalomyocarditis virus and poliovirus, a sixth nucleotide sequence comprising a third coding region, and a seventh nucleotide sequence comprising a poly-A tail, wherein said nucleotide sequences are operably linked such that transcription of the proviral genome gives rise to a messenger RNA molecule comprising transcripts of the said second, third, fourth, fifth, sixth, and seventh nucleotide sequences.

* * * * *

UNITED STATES PATENT AND TRADEMARK OFFICE
CERTIFICATE OF CORRECTION

PATENT NO. : 6,319,707 B1
DATED : November 20, 2001
INVENTOR(S) : M.A. Adam et al.

It is certified that error appears in the above-identified patent and that said Letters Patent is hereby corrected as shown below:

Title page,
Item [73] Assignee "Assignee: Fred Hutchinson Cancer Research Center Board Regents of the University of Washington, Seattle, WA (US)" should read
-- Assignees: Fred Hutchinson Cancer Research Center/Board Regents of the University of Washington, both of Seattle, WA (US) --
Item [56] References Cited after "108:229-241." delete "poliovirus RNA: implications for internal translation initiation. Genes Dev. 3:1026-1034.", after "A cellular protein that binds to the 5'-noncoding region of" insert -- poliovirus RNA: implications for internal translation initiation. Genes Dev. 3:1026-1034. --, "5'noncoding" should read -- 5'noncoding --
Item [57] ABSTRACT, "host cells." should read -- host cells are disclosed. --

Column 1,
Line 8, "HLA41212" should read -- HL41212 --

Column 2,
Line 2, "Otherwise" should read -- Otherwise, --
Line 16, "are favored," should read -- is favored, --

Column 10,
Line 16, "was determined" should read -- were determined --

Column 12,
Line 18, "PNP-Human" should read -- PNP⁻ Human --

Column 13,
Line 2, "ADA-Human" should read -- ADA⁻ Human --

Column 15,
Line 52, "hela" should read -- HeLa --

UNITED STATES PATENT AND TRADEMARK OFFICE
CERTIFICATE OF CORRECTION

PATENT NO. : 6,319,707 B1
DATED : November 20, 2001
INVENTOR(S) : M.A. Adam et al.

It is certified that error appears in the above-identified patent and that said Letters Patent is hereby corrected as shown below:

Column 17,
Line 17, "in a host cell" should read -- in a host cell, --
Line 18, "MoMLV LTR" should read -- MoMLV LTR, --

Signed and Sealed this

Twenty-first Day of May, 2002

Attest:

JAMES E. ROGAN
Attesting Officer    Director of the United States Patent and Trademark Office